United States Patent [19]

Weiss et al.

[11] 4,103,422

[45] Aug. 1, 1978

[54] THREADED SELF-TAPPING ENDODONTIC STABILIZER

[75] Inventors: Charles M. Weiss; Kenneth W. M. Judy, both of New York, N.Y.

[73] Assignee: Oratronics, Inc., New York, N.Y.

[21] Appl. No.: 556,456

[22] Filed: Mar. 7, 1975

[51] Int. Cl.² .............................................. A61C 13/00
[52] U.S. Cl. ..................................................... 32/10 A
[58] Field of Search ................ 32/57, 10 A, 13; 85/46

[56] References Cited

U.S. PATENT DOCUMENTS

| 3,394,626 | 7/1968 | Oliver | 85/46 |
| 3,728,794 | 4/1973 | Edelman | 32/15 |
| 3,813,779 | 6/1974 | Tosti | 32/13 |

*Primary Examiner*—Robert Peshock

*Attorney, Agent, or Firm*—James & Franklin

[57] ABSTRACT

A threaded, self-tapping endodontic stabilizer for insertion into the jawbone of a patient's mouth through an aperture in a loose tooth to stabilize the tooth comprises an elongated penetrating member having adjacent its coronal end a head adapted for manual rotation and adjacent its apical end a threaded shaft defining a plurality of lands and grooves. To promote working and generation of perio-stabilizer ligament, a plurality of the grooves have a longitudinal height of at least 0.20 mm. (preferably about 0.25–0.38 mm.) and extend substantially parallel to the longitudinal axis of the threaded shaft for substantially their entire length intermediate the lands, while a plurality of the lands have a shallow recess extending along the peripheral edge thereof.

6 Claims, 7 Drawing Figures

THREADED SELF-TAPPING ENDODONTIC STABILIZER

BACKGROUND OF THE INVENTION

The present invention relates to an endodontic stabilizer for insertion into the jawbone of the patient's mouth through an aperture in a loose tooth to stabilize the tooth, and more specifically to threaded, self-tapping endodontic stabilizers.

The efficacy of an endodontic stabilizer depends essentially upon three considerations. First, the stabilizer should form an effective apical seal (that is, the seal between the stabilizer and the base of the tooth defining the aperture). Second, the stabilizer must be effectively retained within the tooth to fix the tooth relative to the stabilizer. Third, the stabilizer must be effectively retained within the jawbone beyond the apex to fix the stabilizer relative to the jawbone.

Two types of endodontic stabilizers are currently used in clinical practice — smooth, tapered stabilizers and threaded, self-tapping stabilizers. With smooth, tapered stabilizers, formation of the apical seal is dependent upon effective wedging of the cemented implant at the apex, resistance to implant withdrawal from the tooth is dependent upon the shearing properties of the dental cement employed, and stabilizer retention within the jawbone is dependent upon the formation of collagenous perio-stabilizer ligament about the stabilizer. The smooth, tapered stabilizers have been found to be deficient in all three areas of consideration.

The threaded, self-tapping endodontic stabilizers utilize threads of very low pitch to minimize the torque required for insertion into the tooth dentin during the tapping process. Accordingly, the threads typically define lands of V-shaped cross-section and little, if any, intervening groove area. Such stabilizers thread a portion of the tooth proximal to the apical foramen, and thus provides both a positive apical seal and great resistance to withdrawal forces from the tooth. Indeed, when a tooth specimen has a threaded self-tapping stabilizer properly placed and then removed, examination of the internal surface of the canal will reveal threads in the dentin. Thus threaded, self-tapping stabilizers rate high in the first two areas of consideration (apical seal and retention within the tooth); however they provide little, if any, improvement over the smooth tapered stabilizers when it comes to the third consideration (i.e. the retention of the stabilizer within the jawbone beyond the apex). Generation of perio-stabilizer collagenous ligament adjacent the threads of the stabilizer is minimal, and in fact the ligament over a period of time tends to withdraw from the threaded surface of the stabilizer.

Additional complications occur where the tooth is not only loose, but also broken off coronally, so that an artificial crown must be secured to the stump of the stabilized tooth. Conventional practice in this instance is to use a smooth, tapered stabilizer, and then break off and then remove the upper segment of the stabilizer, leaving the bottom segment to stabilize the tooth. A gold post (sometimes threaded, sometimes unthreaded) is then cemented on the upper portion of the stub above the truncated stabilizer, the upper portion of the gold post serving as a base or secural point for the artificial crown. This procedure has several drawbacks including poor retention of the gold post within the tooth, the extra expense of a gold post, and the extra labor required for breaking of the stabilizer and insertion of the gold post.

Accordingly, it is an object of the present invention to provide a threaded, self-tapping endodontic stabilizer affording a high degree of stabilizer retention within the jawbone beyond the apex.

Another object is to provide such a stabilizer which combines a high degree of retention within the jawbone with an effective apical seal and effective retention within the tooth.

A further object is to provide such a stabilizer for use with a broken tooth, the stabilizer having a head which is adapted to receive an artificial crown thereon.

SUMMARY OF THE INVENTION

It has now been found that the above and related objects are attained in a threaded, self-tapping endodontic stabilizer having a thread design which exercises the perio-stabilizer ligament and thus promotes its retention and bone regeneration adjacent the stabilizer.

Generally speaking, the threaded self-tapping endodontic stabilizer for insertion in the jawbone of the patient's mouth through an aperture in a loose tooth to stabilize the tooth comprises an elongated penetrating member. As is conventional in such stabilizers, the coronal end of the stabilizer comprises a head adapted for manual rotation by the dental practitioner (during the tapping and insertion process), and the apical end comprises a shaft having an external thread defining a plurality of lands and intervening grooves. In order to secure the advantages of the present invention, a plurality of the grooves have a longitudinal height (measured parallel to the shaft axis) of at least 0.20 millimeters, and preferably from 0.25 to 0.38 mm. The aforementioned thread design provides adequate groove surface (between lands) onto which the perio-stabilizer ligament may generate. Once the ligament has generated into the groove areas, the slightest longitudinal motion of the stabilizer exercises and works the portion of the ligament between the lands (in the grooves) and thus encourages further retention and generation of the ligament and bone generation.

Preferably, a plurality of the lands of the thread contain a shallow recess extending along their peripheral edge, the shallow recesses further promoting the working and exercise of the perio-stabilizer ligament by increasing the surface area of the stabilizer, and hence the area of contact between the stabilizer and the ligament.

In an embodiment of the stabilizer suitable for use where the crown of the tooth has been broken off, the head comprises a post integral with the shaft and a rotatable insertion tool removably seated on the post. The post is designed to be engaged by the rotatable insertion tool for rotation therewith, and also to receive thereabout (after removal of the insertion tool therefrom) the interior of an artificial crown. Preferably the post has a pair of substantially planar opposed sides inclined towards the coronal end thereof, and the insertion tool has a pair of correspondingly inclined opposed surfaces which define a recess adapted to receive the coronal end of the post.

DETAILED DESCRIPTION OF THE PREFERRED EMBODIMENTS

Figure 1:
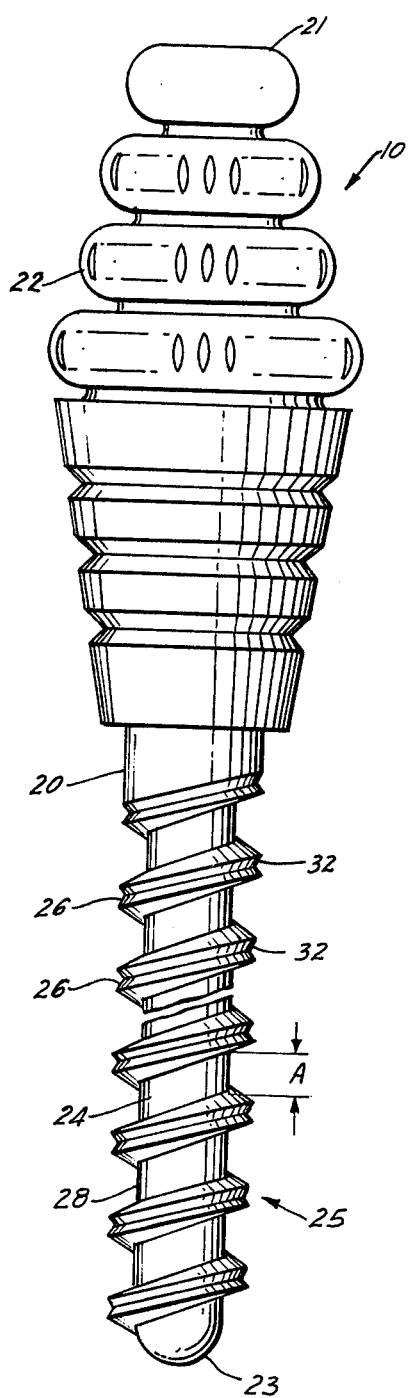
FIG. 1 is a fragmentary side elevation view of a threaded, self-tapping endodontic stabilizer according to the present invention.
Figure 2:
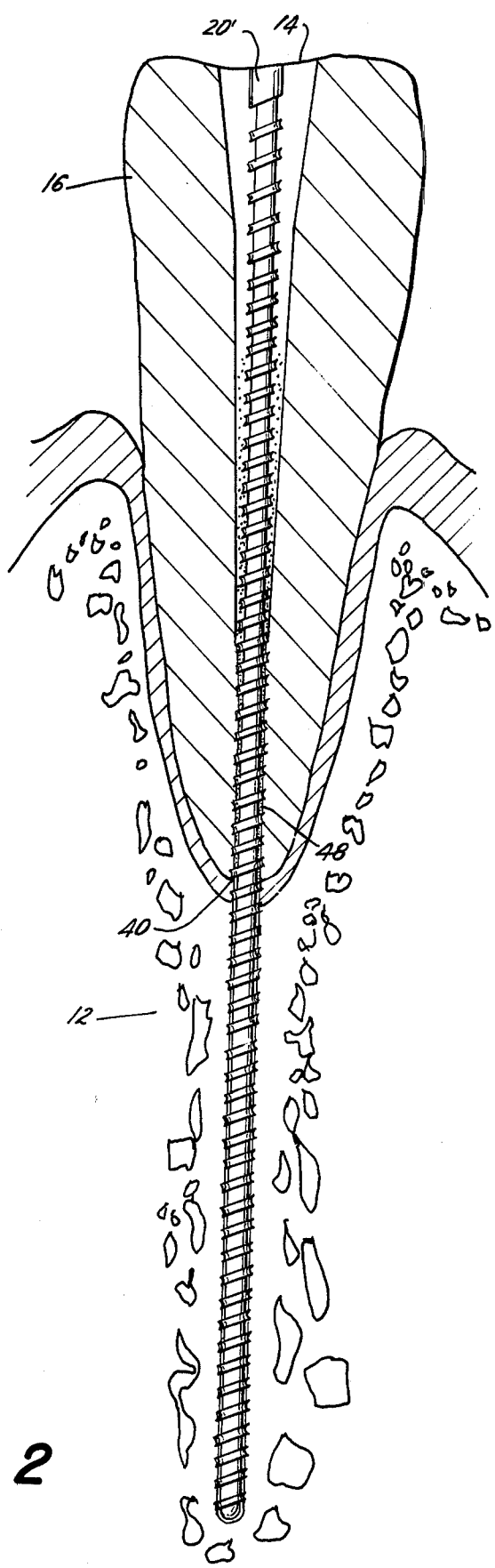
FIG. 2 is an elevation view, partially in cross-section, of a tooth and the surrounding oral environment after the stabilizer of FIG. 1 has been inserted therein and the head of the stabilizer removed.

Referring now to the drawing, and in particular to FIGS. 1 and 2 thereof, therein illustrated is a threaded self-tapping endodontic stabilizer generally designated by the numeral 10 and adapted for insertion into the jawbone 12 of a patient's mouth through an aperture 14 in a loose tooth 16 to stabilize the tooth 16. The stabilizer 10 may be formed of any rigid biocompatible metal of the type commonly used in oral implantology, for example, titanium. More particularly, the stabilizer 10 comprises an elongated penetrating member 20 having adjacent the coronal end 21 thereof a knurled head 22 adapted for manual rotation during the self-tapping and subsequent insertion processes, and adjacent the apical end 23 thereof a shaft 24 of reduced diameter (relative to head 22) having an external thread generally designated by the numeral 25 and defining raised lands 26 and intervening grooves 28.

The stabilizer 10 of the present invention is characterized by a thread 25 in which the groove 28 has a longitudinal height (designated by the reference numeral A in FIG. 1) of at least 0.20 millimeters and preferably about 0.25–0.38 millimeters. The groove 28 preferably extends substantially parallel to the longitudinal axis of shaft 24 for substantially the entire longitudinal height A. Thus adequate space is provided intermediate lands 26 into which perio-stabilizer ligament 30 (see FIG. 5) may generate. Any vertical motion of the stabilizer 10 exercises and works the generated portion of the ligament 30 intermediate lands 26 and thus encourages further generation of the ligament. As the ligament 30 is what effectively secures the stabilizer 10 within the jawbone 12, the overall result is enhanced retention of the stabilizer 10 within the jawbone 12. Grooves having a longitudinal height less than 0.20 millimeters have been found not to afford satisfactory generation of the perio-stabilizer ligament 30 intermediate the jawbone 12 and the shaft 24 because the ligament 30 fails to generate intermediate the closely disposed lands.

It will be noted that as a result of the requirement of a minimum longitudinal height for the groove 28, the pitch of the thread 25 (i.e. the land-to-land longitudinal height) tends to be at least slightly greater in the stabilizer of the present invention than was commonly thought to be desirable. In the past, thread design was determined primarily with a view towards facilitating the tapping operation by reducing the torque required therefor through use of a thread of low pitch. (Less torque was required to effect a single rotation of the stabilizer although more rotations were required). The thread design of the stabilizer of the present invention recognizes the advantages resulting from grooves of greater longitudinal height than were used in the thread design of prior stabilizers, and, accordingly, represents a balance between the consideration of ease of tapping with the consideration of improved retention within the jawbone 12.

The lands 26 preferably have a shallow recess 32 extending along the peripheral edge thereof, so that the lands 26 have a generally W-shaped cross-section. The presence of the recess 32 on the lands 26 increases the surface area of the lands 26, and hence the area of contact between the lands 26 and the perio-stabilizer ligament 30. As a result of the increased area of contact the ligament 30 undergoes increased exercising as a result of any motion on the part of the stabilizer 10.

Figure 3:
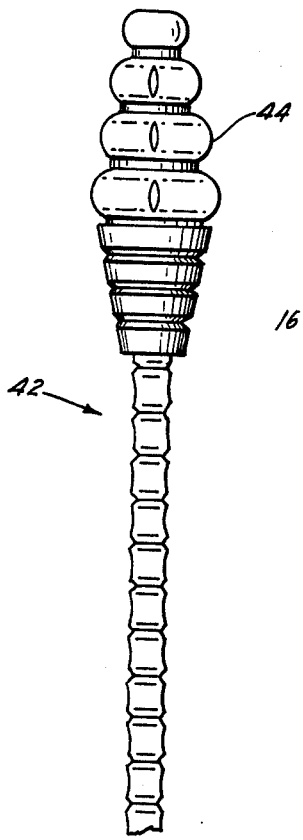
FIG. 3 is a fragmentary elevation view of a measuring rod useful in the procedure for insertion of the stabilizer.

Preparatory to use of the stabilizer 10, an access 14 is prepared in the long axis of the root through the coronal portion of the tooth 16. X-rays may be taken to determine the depth of "available bone" that can accommodate the stabilizer 10, available bone being that bone between the apical foramen or apex 40 and 2–3 millimeters short of the opposite cortical plate (not shown). When the routine endodontic treatment, including bio-mechanical preparation, is completed, the canal is ready for "filling". Hand or mechanical reamers may be used to enlarge the canal to accommodate the pre-selected stabilizer size and a dental drill may be used to precisely parallel the walls of the canal 14 adjacent to the apex 40 and to prepare the stabilizer receptor site in the bone 12 beyond the apex 40. Referring now to FIG. 3, a measuring rod 42 of material opaque to the activating radiation of a radiograph, and having a knurled head 44 adjacent the coronal end and clearly defined segments 46 of known longitudinal length adjacent the apical end (typically millimeter segments), is then introduced into the receptor site in the jawbone and radiographed. From the radiograph, the apical control point can be determined and also the distance in the given units of longitudinal length from the apical point to the proposed stabilizer depth and to the crown of the tooth 16. Additional drilling can alter the depth of the receptor site if necessary. After removal of the measuring rod 42, the pre-selected stabilizer 10 is then rotated by hand about 2 millimeters through the apex 40 to tap the dentin of the tooth 16, after which the stabilizer 10 is reversed out, cleansed and dried.

At this point the canal 14 is cleansed and dried by conventional techniques, for example, by the use of paper points. Cement 48 is then applied to the stabilizer 10 using the apical control point as a guide for cement application. An apical cement is placed on the stabilizer 10 covering 3 millimeters coronal to the apical control point, and a filling cement is applied for the coronal remainder of the stabilizer shaft 24. The stabilizer 10 is then seated with gentle manual rotation. After the cement 48 has hardened, the disposable head 22 and any unused portion of the shaft 24 may be severed (for example, by drilling) to leave a truncated stabilizer 20, as illustrated in FIG. 2. The opening or access 14 of the tooth 16 is then ready to be sealed following customary oral implantology practice.

Figure 6:
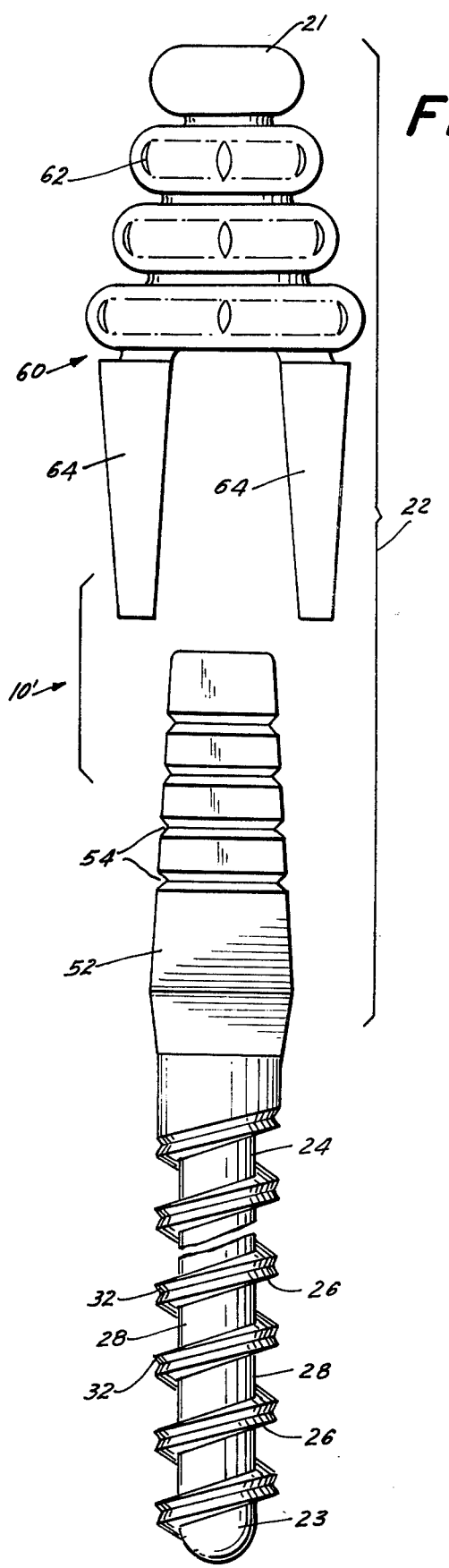
FIG. 6 is an exploded elevation view of a stabilizer according to the present invention including a removable insertion tool.
Figure 7:
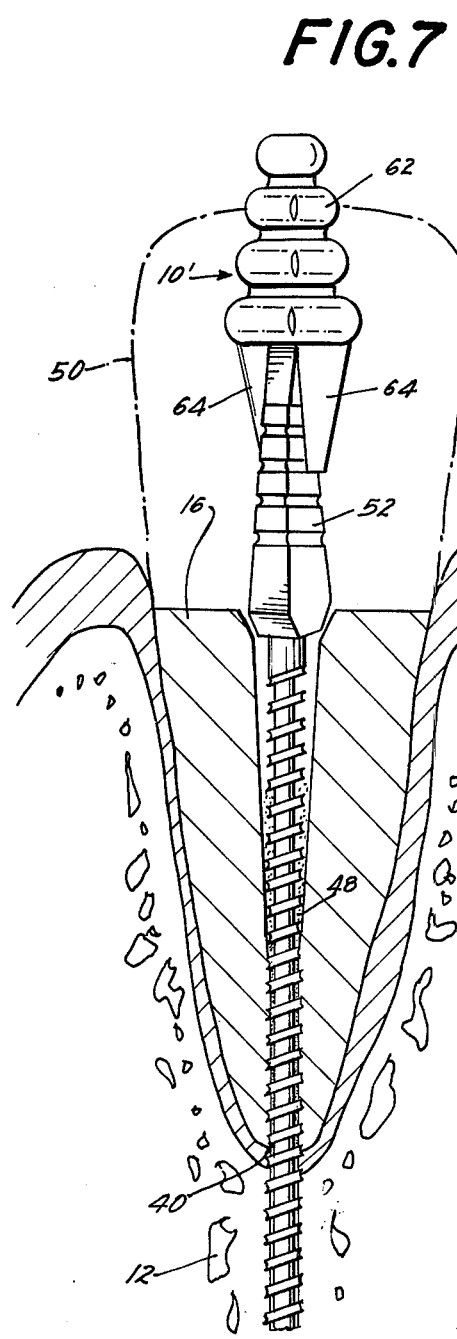
FIG. 7 is an elevation view, partially in cross-section, of the stabilizer of FIG. 6 in its ultimate oral environment, with an artificial crown illustrated in phantom line as secured on the post thereof.

Referring now to FIGS. 6 and 7, therein illustrated is a stabilizer 10′ adapted for use where the crown portion of the tooth 16 has been broken away or otherwise removed and will eventually be replaced by an artificial crown or cap 50 (as illustrated in phantom line in FIG. 7). The stabilizer 10' is identical in all respects to the stabilizer 10 of FIGS. 1 and 2, except for the head 22 thereof. In this embodiment the head comprises a post 52 integral with the shaft 24 and adapted to receive thereabout the interior of the artificial crown 50. The opposed sides of the post 52 forming the coronal end 21 of the penetrating member 20 are essentially planar and tapered inwardly toward the coronal end 21. Various equidistantly spaced shallow grooves 54 may extend horizontally along the periphery of the post 52 as measurement references. While both pairs of opposed sides of post 52 have been illustrated as substantially planar and inwardly tapering, it is only essential that a pair of the post sides, preferably the long sides, have planar surfaces.

The head 22 further includes a rotatable insertion tool generally designated by the numeral 60 and comprising a knurled upper portion 62 to facilitate rotation thereof and a pair of depending legs 64. The inner surfaces of the legs 64 are essentially planar and tapered outwardly to define there between a recess adapted to receive the post 52 therein. When the insertion tool 60 is properly seated on the post 52, the inclined surfaces of legs 64 are adjacent a correspondingly inclined pair of surfaces of post 52, so that rotation of the upper portion 62 of the insertion tool 60 causes a corresponding rotation of post 52 and hence the entire stabilizer 10'.

The stabilizer 10' of FIGS. 6 and 7 is utilized in precisely the same manner as the stabilizer 10 of FIGS. 1 and 2, except that the excess length thereof is removed from the apical end 23 prior to insertion and cementing to enable the apical end of the post 52 to seat against the faced off root surface. Removal of the insertion tool 62 after insertion exposes the post 52. After hardening of the cement 48, an artificial crown 50 may be secured directly to the post 52 by conventional dental techniques, thus providing an artificial crown 50 for the tooth 16 without resort to the costly and laborious prior art technique requiring removal of a stabilizer head and insertion of a gold post.

Figure 4:
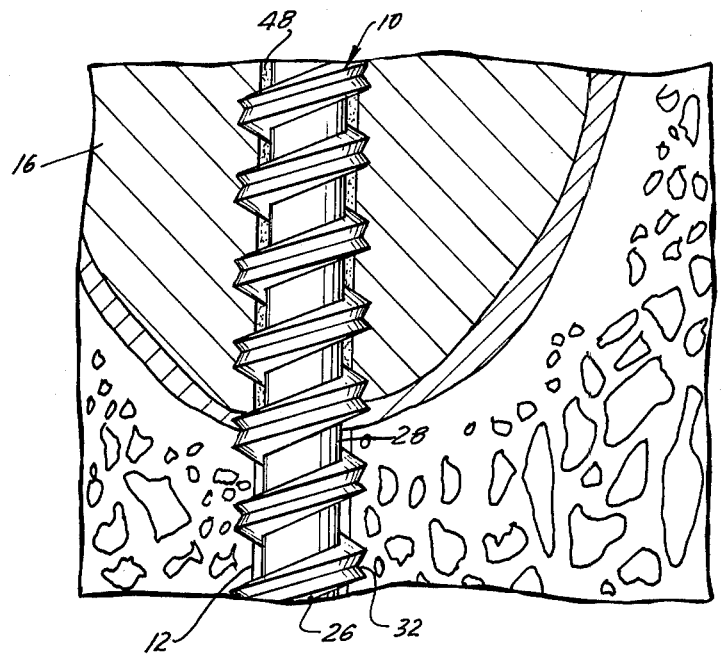
FIG. 4 is a fragmentary elevation view, partially in cross-section, of the stabilizer of FIG. 1 and its immediate environment shortly after insertion.
Figure 5:
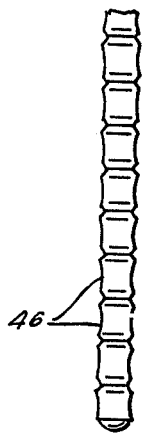
FIG. 5 is a fragmentary elevation view, partially in cross-section, of the stabilizer of FIG. 1 and its immediate environment after generation of the perio-stabilizer ligament and regeneration of surrounding bone.
Figure 5:
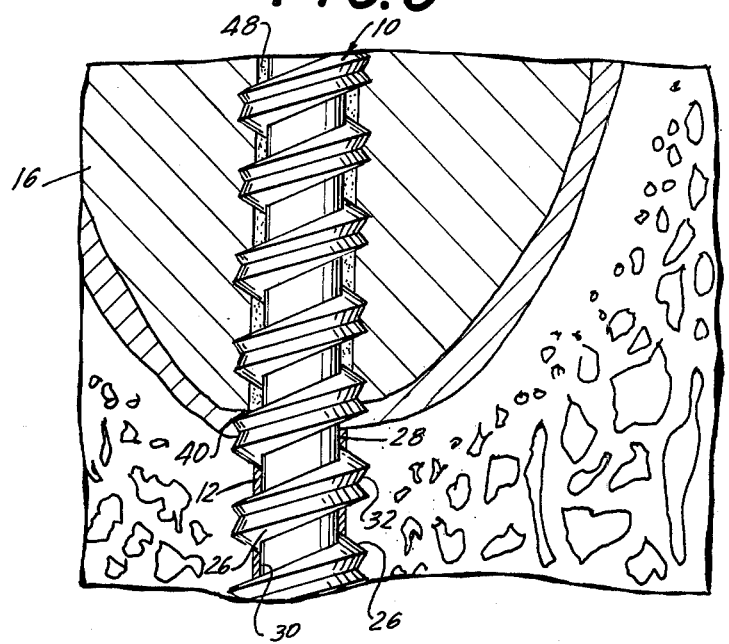

The advantages accruing from the stabilizer of the present invention are readily apparent from a comparison of FIGS. 4 and 5 which illustrate the truncated stabilizer 10 and its immediate oral environment shortly after insertion and after healing (i.e. 4–6 weeks after insertion), respectively. In FIG. 4, the bone 12 adjacent the lower end of the stabilizer 10 (below the apical foramen 40) conforms generally to the periphery of the stabilizer 10, but is relatively thin and weak. In FIG. 5, perio-stabilizer ligament 30 has been generated intermediate the bone 12 and the grooves 28. Continuous exercise of the perio-stabilizer ligament 30 due to its entrapment within the grooves 28 and intermediate the lands 26, and also due to the enhanced surface area of contact due to the recesses 32, has resulted in a thickening and strengthening of bone 12 which now extends closer to the grooves 28. Thus, the stabilizer of the present invention not only forms a positive apical seal and affords desirable retention of the stabilizer within the tooth, but also affords an effective retention of the stabilizer within the jawbone not previously afforded by the prior art stabilizers.

Now that the preferred embodiments of the present invention have been shown and described in detail, various modifications and improvements thereon will become readily apparent to those skilled in the art. Accordingly, the spirit and scope of the present invention is to be limited only by the appended claims, and not by the foregoing disclosure.

We claim:

1. In a threaded, self-tapping endodontic stabilizer for insertion into the jawbone of a patient's mouth through an aperture in a loose tooth to stabilize the tooth comprising an elongated penetrating member having adjacent its coronal end a head adapted for manual rotation and adjacent its apical end a threaded shaft defining a plurality of lands and grooves, the improvement wherein a plurality of said grooves have a longitudinal height of at least 0.20 mm. and a plurality of said lands have a shallow recess extending along the peripheral edge thereof.

2. The stabilizer of claim 1 wherein a plurality of said grooves have a longitudinal height of 0.25–0.38 mm and extend substantially parallel to the longitudinal axis of said threaded shaft intermediate said lands, and a plurality of said lands have a shallow recess extending along the peripheral edge thereof.

3. The stabilizer of claim 1 wherein said threaded shaft comprises a shaft of constant diameter and an external thread thereon.

4. The stabilizer of claim 2 wherein each of said grooves intermediate said lands has a longitudinal height of 0.25–0.38 mm and extends longitudinally parallel to the longitudinal axis of said threaded shaft intermediate said lands and wherein each of said lands intermediate said grooves has a shallow recess extending along the peripheral edge thereof.

5. The stabilizer of claim 4 wherein said threaded shaft comprises a shaft of constant diameter and an external thread thereon.

6. In a threaded, self-tapping endodontic stabilizer for insertion into the jawbone of a patient's mouth through an aperture in a loose tooth to stabilize the tooth comprising an elongated penetrating member having adjacent its coronal end a head adapted for manual rotation and adjacent its apical end a threaded shaft defining a plurality of lands and grooves, the improvement wherein a plurality of said grooves have a longitudinal height of at least 0.20 mm., said head comprises a post integral with said shaft and adapted to receive thereabout the interior of an artificial crown and a rotatable insertion tool removably seated on said post for rotation of said post therewith, said post has a pair of substantially planar sides inclined toward its coronal end, and said insertion tool has a pair of correspondingly inclined opposed surfaces adjacent its apical end defining a recess adapted to receive the coronal end of said post.

* * * * *